(12) United States Patent
Reichow et al.

(10) Patent No.: US 8,513,055 B2
(45) Date of Patent: *Aug. 20, 2013

(54) UNITARY VISION AND COORDINATION TESTING CENTER

(75) Inventors: Alan W. Reichow, Beaverton, OR (US); Ryan C. Coulter, Portland, OR (US)

(73) Assignee: Nike, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/595,209

(22) PCT Filed: Apr. 14, 2008

(86) PCT No.: PCT/US2008/060244
§ 371 (c)(1),
(2), (4) Date: Mar. 24, 2010

(87) PCT Pub. No.: WO2008/128187
PCT Pub. Date: Oct. 23, 2008

(65) Prior Publication Data
US 2010/0177278 A1     Jul. 15, 2010

Related U.S. Application Data

(60) Provisional application No. 60/923,434, filed on Apr. 13, 2007, provisional application No. 60/941,915, filed on Jun. 4, 2007.

(51) Int. Cl.
*H01L 21/00* (2006.01)
*A61B 3/00* (2006.01)
*A61B 3/10* (2006.01)

(52) U.S. Cl.
USPC .......... 438/106; 351/203; 351/205; 351/211; 351/221; 351/246

(58) Field of Classification Search
USPC ................ 351/203, 200–201, 205, 211, 221, 351/246, 222, 237
See application file for complete search history.

(56) References Cited

U.S. PATENT DOCUMENTS

| 3,861,790 A | 1/1975 | Tamura |
| 4,528,989 A | 7/1985 | Weinblatt |

(Continued)

FOREIGN PATENT DOCUMENTS

| JP | 6217938 | 8/1994 |
| JP | 6237895 | 8/1994 |

(Continued)

OTHER PUBLICATIONS

International Search Report and Written Opinion for PCT/US08/60229, Mailed Sep. 9, 2008, 9 Pages.

(Continued)

*Primary Examiner* — Dawayne A Pinkney
(74) *Attorney, Agent, or Firm* — Shook, Hardy & Bacon L.L.P.

(57) ABSTRACT

System and methods for testing and/or training a subject's vision and coordination abilities are provided. More specifically, the method may include testing various aspects of the subject's vision and coordination abilities, such as eye-hand coordination, split attention, reaction time, body coordination, etc. By using various tests, an efficient examination may be administered. In accordance with the invention, an individual may be subjected to such a method of testing and/or training at a unitary center capable of presenting such tests to the individual, receiving input from the individual, and processing the received input. Such a unitary test center may further be configurable, so that the tests administered may vary based on the needs of the individual. The received input may then, for example, be used to compute data related to the user's vision and coordination abilities, both overall and for each individual test.

17 Claims, 4 Drawing Sheets

(56) References Cited

U.S. PATENT DOCUMENTS

| | | | |
|---|---|---|---|
| 5,050,982 A | 9/1991 | Meissner | |
| 5,088,810 A | 2/1992 | Galanter | |
| 5,478,239 A | 12/1995 | Fuerst | |
| 5,812,239 A | 9/1998 | Eger | |
| 5,825,460 A | 10/1998 | Kohayakawa | |
| 5,919,149 A | 7/1999 | Allum | |
| 6,092,058 A | 7/2000 | Smyth | |
| 6,261,239 B1* | 7/2001 | Abraham-Fuchs et al. | 600/558 |
| 6,267,733 B1 | 7/2001 | Peterson et al. | |
| 6,364,845 B1 | 4/2002 | Duffy et al. | |
| 6,371,931 B1 | 4/2002 | Guillen | |
| 6,632,174 B1 | 10/2003 | Breznitz | |
| 6,755,525 B2 | 6/2004 | Reichow | |
| 6,796,927 B2 | 9/2004 | Toyama | |
| 6,811,258 B1 | 11/2004 | Grant | |
| 6,893,127 B2 | 5/2005 | Reichow | |
| 7,073,208 B2 | 7/2006 | Penque | |
| 7,326,060 B2 | 2/2008 | Seiller et al. | |
| 7,849,115 B2* | 12/2010 | Reiner | 707/912 |
| 2003/0120183 A1 | 6/2003 | Simmons | |
| 2003/0211449 A1 | 11/2003 | Seiller et al. | |
| 2004/0141152 A1 | 7/2004 | Marino et al. | |
| 2005/0053904 A1 | 3/2005 | Shephard | |
| 2005/0273017 A1 | 12/2005 | Gordon | |
| 2006/0161218 A1 | 7/2006 | Danilov | |
| 2006/0195018 A1 | 8/2006 | Guillen | |
| 2006/0244915 A1 | 11/2006 | Clemons et al. | |
| 2006/0251334 A1 | 11/2006 | Oba et al. | |
| 2006/0287617 A1 | 12/2006 | Taub | |
| 2007/0000007 A1 | 1/2007 | MacDonald | |
| 2007/0013870 A1* | 1/2007 | Hara et al. | 351/237 |
| 2007/0052674 A1 | 3/2007 | Culver | |
| 2007/0254270 A1 | 11/2007 | Hersh | |
| 2008/0003553 A1 | 1/2008 | Stark et al. | |
| 2009/0093305 A1 | 4/2009 | Okamoto et al. | |
| 2009/0129205 A1 | 5/2009 | Reichow | |
| 2009/0130640 A1 | 5/2009 | Hardy | |
| 2009/0150919 A1 | 6/2009 | Lee | |

FOREIGN PATENT DOCUMENTS

| | | |
|---|---|---|
| JP | 7299033 | 11/1995 |
| JP | 10305016 | 11/1998 |
| JP | H 11225961 | 2/1999 |
| JP | 11267101 | 10/1999 |
| JP | 11318824 | 11/1999 |
| JP | 2003126036 | 5/2003 |
| JP | 2004135756 | 5/2004 |
| WO | 200017615 | 3/2000 |
| WO | 2004006747 | 1/2004 |
| WO | 2006029048 | 3/2006 |
| WO | 2006088415 | 8/2006 |
| WO | 2007009990 A1 | 1/2007 |
| WO | 2008128192 | 10/2008 |

OTHER PUBLICATIONS

Supplementary European Search Report for EP08745763, Completed Jun. 16, 2010, 9 Pages.

Rouse, et al., "A Comparison Study of Dynamic Visual Acuity Between Athletes and Nonathletes", Journal of the American Optometric Association, Dec. 1988, pp. 946-950, vol. 59, No. 12, United States.

Coffey, et al., "Optometric Evaluation of the Elite Athlete," Problems in Optometry, Mar. 1990, pp. 32-59, vol. 2, No. 1, United States.

Reichow, et al., "Introduction to Behavioral Optometry", Sports Vision, 1993, 75 pages, Optometric Extension Program Foundation, United States.

Reichow, et al., "A Comparison of Contrast Sensitivity in Elite Athletes Versus a Normal Population", American Journal of Optometry and Physiological Optics, Dec. 15, 1986, vol. 63, No. 82, United States.

Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.

Herdman, et al., "Computerized Dynamic Visual Acuity Test in the Assessment of Vestibular Deficits", The American Journal of Otology, 1998, pp. 790-796, vol. 19, No. 6, United States.

Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.

"Coffey, et al., "Visual Performance Enhancement in Sports Optometry"", Sports Vision 1995, pp. 158-177, Butterworth-Heinermann, United States.

Ferreira, "An Overview of Research in Sports Vision: its History and an Optometric Perspective", The South African Optometrist, Dec. 2003, pp. 142-149, vol. 62, No. 4, Auckland Park, South Africa.

Koenig, "Practicing Perception: Eyes Can Be Trained to be More Effective", USA Today Baseball Weekly, 1996, 3 pages, United States.

International Search Report and Written Opinion for PCT/US08/60249, Mailed Sep. 8, 2008, 9 Pages.

Supplementary European Search Report for EP08745783, Completed Jun. 23, 2010, 10 Pages.

International Search Report and Written Opinion for PCT/US08/60244, Mailed Sep. 4, 2008, 9 Pages.

Supplementary European Search Report for EP08745778.4, Completed Jun. 23, 2010, 9 Pages.

Supplementary European Search Report for EP08780526, Completed Jun. 16, 2010, 11 Pages.

International Search Report and Written Opinion for PCT/US08/60252, Mailed Aug. 15, 2008, 10 Pages.

International Search Report and Written Opinion for PCT/US09/043127, Mailed Jul. 6, 2009, 11 Pages.

Cardall, "Contact Lenses in Sport: a General Overview", Optician, Jan. 13, 2006, pp. 22-25, vol. 231, No. 6034, United States.

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.

International Search Report and Written Opinion for PCT/US2010/041564, Mailed Nov. 12, 2010.

Office Action of Jan. 6, 2011 in U.S. Appl. No. 12/117,315, 16 pages.

Final Office Action of May 26, 2011 in U.S. Appl. No. 12/117,315, 10 pages.

Non-Final Office Action in U.S. Appl. No. 12/500,385 mailed Mar. 19, 2012, 39 pages.

Office Action in U.S. Appl. 12/595,208 mailed Nov. 28, 2011, 20 pages.

Notice of Allowance and Fees Due in U.S. Appl. No. 12/595,207 mailed Apr. 12, 2012, 79 pages.

Final Office Action in U.S. Appl. No. 12/595,208 mailed May 10, 2012, 25 pages.

Final Office Action in U.S. Appl. No. 12/500,385 mailed Nov. 6, 2012, 43 pages.

EP Office Action Application No. 08 780 526.3-2319 Dated Nov. 28, 2012.

A. Ludeke, et al., "The difference in visual skills between professional versus non-professional rugby players" The South African Optometrist, Dec. 1, 2003 pp. 150-158, XP055044423.

Martjin LTM Muller:"Attentional components of postural control" Dissertation, 2007, XP055044427, Saline MI (USA) Retrieved from the Internet: URL: http://dare.uva.n./document/48212 [retrieved on Nov. 15, 2012].

* cited by examiner

UNITARY VISION AND COORDINATION TESTING CENTER

CROSS-REFERENCE TO RELATED APPLICATIONS

This application claims priority to U.S. Provisional Application No. 60/923,434 filed on Apr. 13, 2007, entitled "System and Method for Testing Visual Ability During Simulated Activity," which is hereby incorporated by reference. This application also claims priority to U.S. Provisional Application No. 60/941,915 filed on Jun. 4, 2007, entitled "System and Method for Decoupled Visual Ability Testing," which is hereby incorporated by reference.

STATEMENT REGARDING FEDERALLY SPONSORED RESEARCH OR DEVELOPMENT

Not applicable.

TECHNICAL FIELD

The present invention relates generally to the evaluation and/or training of an individual's vision and coordination.

BACKGROUND OF THE INVENTION

Along with physical ability, an individual's sight plays a role in the individual's performance when participating in an activity, such as a sport. Typically, to improve in the sport or activity, an individual will focus on improving their physical ability to elevate their overall performance. By testing and training the individual's vision and coordination abilities or acuity, however, the individual's performance may also improve.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with the invention, a method of testing and/or training a subject's vision and coordination abilities is provided. More specifically, the method may include testing various aspects of the subject's vision and coordination ability at a unitary testing center. By using various tests, a more streamlined examination may be administered. In accordance with the invention, an individual may be subjected to such a method of testing and/or training at a unitary center capable of presenting vision and coordination tests to the individual, receiving input from the individual, and processing the received input. Such a unitary test center may further be configurable, so that the tests administered may vary based on the needs of the individual. The received input may then, for example, be used to compute data related to the user's vision and coordination ability, both overall and for each individual test.

BRIEF DESCRIPTION OF THE DRAWINGS

The present invention is described in detail below with reference to the attached drawing figures, wherein.

DETAILED DESCRIPTION OF THE INVENTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

In accordance with the present invention, systems and methods for testing a subject's vision and coordination abilities at a unitary testing unit are provided. Such a method may include testing various aspects of the subject's vision and coordination abilities (e.g., eye-hand coordination, split attention, reaction time, body coordination, etc.) at a unitary testing unit that may also be capable of processing the resulting data and/or transmitting data over a network to another location for processing. In doing so, the unitary testing center may streamline the process of testing the vision and coordination abilities of subject, and may reduce overhead (e.g., reduce the equipment) needed to perform testing. Additionally, the unitary testing center may be configurable, so that the tests administered may vary based on the needs of the individual. The received input may then, for example, be used to compute results related to the user's vision and coordination abilities, both overall and for each individual test.

In one embodiment, a testing device for testing the vision and coordination ability of a subject is provided. Such a testing device may include a presenting component, an input component, and a processing component, where the presenting component is capable of presenting a visual clarity test, a contrast sensitivity test, a visual tracking test, a distance focusing test, and a visual aiming test to the subject. In response to each test, the subject may provide input to the testing device. The input component may then be configured to receive the input, and the processing component may be configured to process the received input.

In another embodiment, a method for testing the vision and coordination abilities of a subject, where the method occurs at a unitary location, is provided. The method comprises, in part, administering two or more vision ability tests to the test subject; receiving input from the test subject in response to each test; and processing the input received from the test subject.

Figure 1:
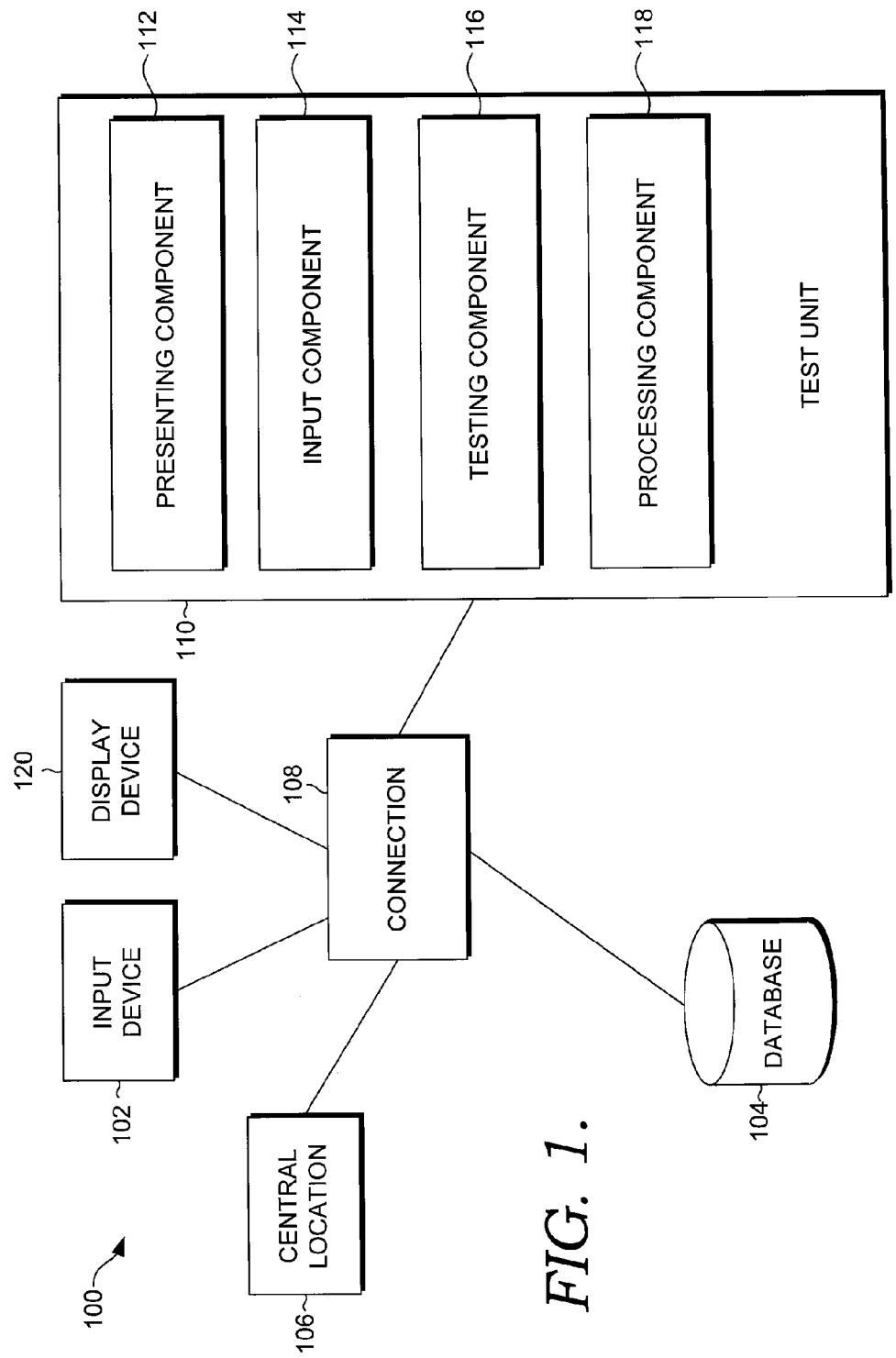
FIG. 1 is a block diagram of a computing system environment suitable for use in implementing the present invention.

Referring to the drawings in general, and initially to FIG. 1 in particular, a block diagram of an exemplary computing system is shown and designated generally as computing system 100 configured to provide for testing the visual and coordination abilities of a subject. It will be understood and appreciated by those of ordinary skill in the art that the computing system 100 shown in FIG. 1 is merely an example of one suitable computing system environment and is not intended to suggest any limitation as to the scope of use or functionality of embodiments of the present invention. Neither should the computing system 100 be interpreted as having any dependency or requirement to any single component or combination of components illustrated therein.

The computing system 100 includes an input device 102, a display device 120, a database 104, a central location 106, and a test unit 110, all in communication with one another via a connection 108. The connection 108 may be made by wire (such as a cable), or wireless (such as a wireless network). Connection 108 may also be a network, where the network may include, without limitation, one or more local area networks (LANs) and/or wide area networks (WANs). Such networking environments are commonplace in enterprise-wide computer networks, intranets, and the Internet. Further, the connection 108 may comprise a locally wired connection between components of computing system 100. Accordingly, the connection 108 is not further described herein.

The input device 102 is capable of receiving one or more responses from a subject. Input device 102 may be any device that may receive responses from a subject. One skilled in the art will appreciate that more than one input device, such as input device 102, may be used with computing system 100. Input device 102 may be, for example, a microphone, joystick, game pad, wireless device, keyboard, keypad, game controller, treadmill, force plate, eye tracking system, gesture recognition system, touch sensitive screen, and/or any other input-initiating component that provides wired or wireless data to the test unit 110, which may be received through the network 108. Input device 102 may include voice recognition equipment and/or software that processes auditory inputs from the test subject. For example, the auditory input from the subject, in order to show recognition of the visual indicia, may be a verbalization of the trait possessed by the visual indicia. In one embodiment, if the trait is a direction orientation of a Landolt "C," the responsive auditory inputs may be "up," "down," "right," and "left." However, one skilled in the art will understand and appreciate that other auditory inputs may be used (e.g., stating a color, numeral, letter, symbol, etc.) to indicate that the subject perceived and/or recognized the visual indicia. It should be noted, however, that the present invention is not limited to implementation on such input devices 102, but may be implemented on any of a variety of different types of devices within the scope of embodiments hereof. Input indicating the subject's response to a displayed visual indicia may be received and captured with input device 102. If the trait is a directional orientation, a satisfactory test response may be identifying the direction that the visual indicia is facing. By way of example only, without limitation, identifying may include the subject providing input by manipulating a joystick in a direction corresponding to the directional orientation on a hand-held device employed as the input device 102.

If input device 102 is an eye tracking system, the position and/or focus of the eyes of subject may be monitored and an input registered when the eyes are positioned and/or focused at the proper location.

If input device 102 is a gesture recognition system, a variety of systems and/or methods may be used to receive inputs. For example, one or more cameras may be used to monitor the movement of a subject's body limbs and/or extremities and, in conjunction with appropriate hardware and/or software, register an input when subject makes an appropriate gesture. Gesture recognition systems may also utilize optical markers attached to subject to facilitate motion tracking. Transmitters attached to subject and receivers (for example, utilizing radio infrared, sonic, subsonic, or ultrasonic transmissions) may also be utilized as part of a gesture recognition system.

If input device 102 is a touch sensitive screen, any type of touch sensitive screen may be utilized. Also, an overlay of a touch sensitive material may be used to receive touch inputs in conjunction with a display that is not itself touch sensitive. Such an overlay may be any distance from the display.

The display device 120 may be capable of displaying output video visually observable by a subject and may be any type of computer, testing apparatus, or television monitor, including cathode ray tube, liquid crystal display, plasma screen, or any other display type, or may comprise a screen upon which images are projected, either from the front or from the rear. Further, the display device 120 may provide a user interface for a test administrator to interact with the test unit 110 before, during, and after administering the vision ability tests to a test subject.

The test unit 110, as shown in FIG. 1, may be any type of computing device, embodiments of which will be more fully discussed below with reference to FIGS. 4 and 5. The database 104 may be configured to store information associated with tests of vision and coordination abilities. It will be understood and appreciated by those of ordinary skill in the art that the information stored in the database 104 may be configurable and may include any information relevant to the testing of vision and coordination abilities. The content and volume of such information are not intended to limit the scope of embodiments of the present invention in any way. Although illustrated as a single, independent component, database 104 may, in fact, be a plurality of database, for instance, a database cluster. Further, portions or the entirety of the database 104 may reside on a computing device associated with the test unit 110, another external computing device (not shown), and/or any combination thereof. One skilled in the art should appreciate that database 104 is optional and need not be implemented in conjunction with the computing system 100.

Returning to FIG. 1, the test unit 110 may include a presenting component 112, an input component 114, a testing component 116, and a processing component 118, shown in accordance with an embodiment of the present invention. It will be understood by those of ordinary skill in the art that the components 112, 114, 116, and 118 illustrated in FIG. 1 are exemplary in nature and in number, and should not be construed as limiting. Any number of components may be employed to achieve the desired functionality within the scope of embodiments of the present invention.

The presenting component 112 may be capable of displaying output video visually observable by a subject and may be any type of computer, testing apparatus, or television monitor, including cathode ray tube, liquid crystal display, plasma screen, or any other display type, or may comprise a screen upon which images are projected, either from the front or from the rear.

In one embodiment, presenting component 112 may be an apparatus that uses mirror and/or lenses strategically placed to generate a visual perspective of distance within a limited spatial area (e.g., providing a periphery configuration of mirrors to produce a tunnel effect). An example of such an apparatus is a perspective testing apparatus utilizing mirrors to generate a perspective of distance. Such an apparatus may include a mirror that displays the visual indicia in a central foveal area (i.e., directly in front of the subject), and may further include side mirrors that display a visual indicia to test peripheral visual ability.

In another embodiment, an apparatus may include lenses that change perceived distance and/or size of the displayed visual indicia to achieve a simulated distance. As a result, such an apparatus may provide a displayed visual indicia that appears to the test subject to be nearer or farther than the actual display. Thus, this configuration creates the perspective of optical infinity to the test subject.

One skilled in the art will appreciate that presenting component 112 may comprise multiple devices that, in combination, display some of the visual stimuli typical for a particular activity. In one embodiment, a single device may be used to display multiple displays of visual indicia (e.g., split-screen).

Presenting component 112 may alternatively comprise display glasses, goggles, visors, and the like, that may be worn by a subject to provide a visual display for the subject that is not typically visible to others. Additionally, presenting component 112 may provide a two dimensional or three dimensional image to the test subject. The three dimensional image display may include virtual reality or holographic presentations to the subject.

In operation, the presenting component 112 may be configured to present one or more visual indicia to a test subject. As discussed more fully below, presenting component 112 may present visual indicia in varying ways to test different aspects of the subject's vision and coordination abilities. In general, each of the visual indicia may possess a trait or traits. This trait may be, for example, a directional orientation (e.g., arrow, Landolt "C", Tumbling E, etc.), a position on a user interface (e.g., located in a particular quadrant of the display), one of a predetermined number of mutually exclusive traits (e.g., indicator that faces either up, down, left, or right), or any combination of traits. Further, one of ordinary skill in the art will understand and appreciate that other traits may be used, and the present invention is not limited to any particular trait.

The input component 114 may be configured to receive input from the test subject (e.g., by utilizing input device 102). Any suitable receiving component that is capable of receiving input provided by the subject may be used in accordance with this invention. By way of example, without limitation, the subject may provide input utilizing a keyboard, joystick, trackball, or the like. The input may depend upon the presenting component. For example, if the presenting component is touch-sensitive, the subject could provide input by touching the presenting component. In another embodiment, the input component could have voice recognition capability, where the subject may provide input with a vocalized response that is recognized by the input component. One skilled in the art will understand and appreciate that any suitable input component may be used in accordance with the present invention. Certain types may be preferred based on the tests presented by the presenting component and, as discussed above, the capabilities of the presenting component. After receiving input from the subject, the input component 114 may store the input, for instance, in database 104 for future reference.

The testing component 116 is configured to provide tests to the subject. As will be discussed more fully below with respect to FIG. 2, testing component 116 may provide two or more tests to determine the vision and coordination abilities of a subject. More specifically, multiple tests may be provided at a unitary location, such as test unit 110. Further, testing component 116 is configurable so that the tests may vary depending on the subject. For example, the tests may vary given the test subject's particularized sport or activity, competition level, visual strengths/weaknesses, etc. Thus, the testing component 116 may also be responsible for determining the tests (and level or difficulty of tests) presented by the presenting component 112.

Figure 3:
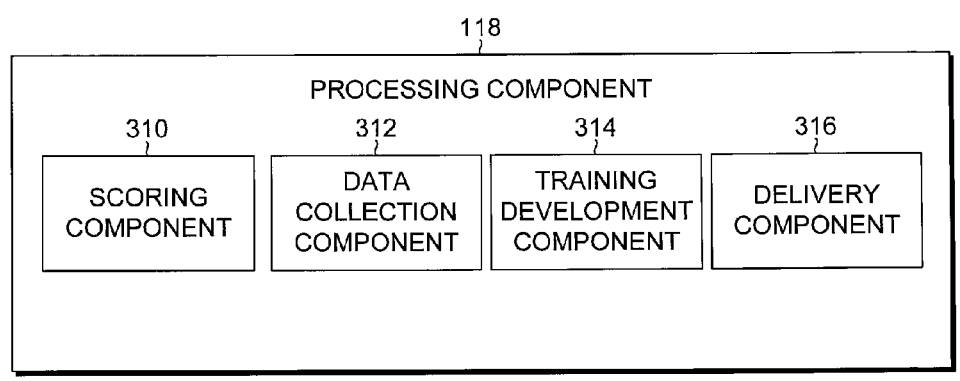
FIG. 3 illustrates a block diagram of an exemplary processing component for use in implementing the present invention.

The processing component 118 is provided to process the input received by input component 114. As shown in FIG. 3, the processing component 118 may comprise a scoring component 310, a data collection component 312, a training development component 314, and a delivery component 316. The scoring component 310 may be configured to utilize a scoring algorithm to derive a score based on the subject's response to the tests presented. The subject's responses may be determined by comparing such response to those from a particular population, typically retrieved from the database 104. The scoring component 310 may provide an evaluation of the vision and coordination abilities of the subject incident to receiving and measuring one or more responses to the visual indicia. Once a score (e.g., percentile) is determined, it may be presented to the subject via presenting component 112. The score may be presented at the conclusion of each test, at the conclusion of all tests, or a combination thereof.

The data collection component 312 is configured to collect the data received from input component 114. Such data may then be stored, for example, in database 104. The data collected may further be used to create standards for a particular population, which may then be used by scoring component 310. One of skill in the art will appreciate that database and 104 and/or scoring component 310 may be located remotely from other components of system 100.

The training development component 314 is configured to develop a training plan or regimen for the test subject based on the collected data and determined scores. In embodiments of the present invention, test unit 110 may be used for training the test subject, after the subject has undergone testing.

The delivery component 316 is configured to transmit the determined score, collected data, and the like to presenting component 112. The delivery component 316 may additionally provide this data to an external computing device, such as central location 106, for further consideration, analysis, or storage. In one embodiment, the delivery component 316 may provide data in real time to testing component 116, such that the tests may be configured or varied while still in the testing process. It should be understood and appreciated by those of ordinary skill in the art that, although embodiments and examples are discussed above, the delivery component 316 may provide information related to testing vision and coordination abilities to any component of the computing system 100, both internal and external to the test unit 110.

One skilled in the art will appreciate that the delivery component 316 may send information from test unit 110 at any desired frequency. That is, the information may be sent to a desired location, for example, after a subject completes all tests or, alternatively, after each individual test. If sending the information to central location 106 or database 104 for storage and/or processing, the information may be sent collectively for all subjects at the end of the day. The frequency may depend upon the storage capacity and processing capability of the test unit 110, as well as the desired use of the information.

Figure 2:
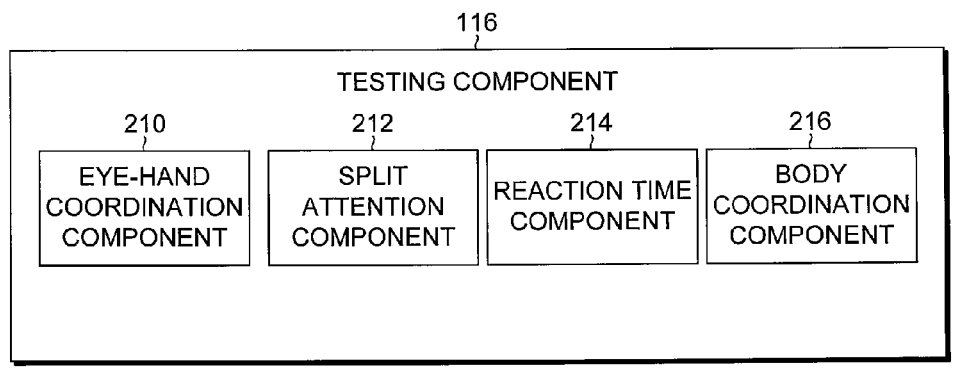
FIG. 2 illustrates a block diagram of an exemplary testing component for use in accordance with an embodiment of the present invention.

Referring now to FIG. 2, testing component 116 is further illustrated. Testing component 116 may comprise an eye-hand coordination component 210, a split attention component 212, a reaction time component 214, a body coordination component 216, and/or any other type of visual testing component. Each of these components may be used by test unit 110 to test various aspects of an individual's vision and coordination abilities. One skilled in the art will appreciate that other tests may be used and are within the scope of the invention.

The eye-hand coordination component 210 is configured to test the visual clarity of a subject, and may include displaying a visual indicia in different locations and requiring the test subject to locate the visual indicia at each location. Any visual indicia may be used. In one embodiment, the visual indicia may be presented using a display device as the presenting component 112, where the display device is touch sensitive and thus also serves as an input device. In such an embodiment, the test subject may locate the visual indicia by touching the display device, and this response is inputted into the test unit 110. One skilled in the art will appreciate and understand that any suitable test that tests a subject's eye-hand coordination may be used by the eye-hand coordination component 210.

The split attention component 212 is configured to test the coordination of a test subject while focusing on a visual indicia in a different location. In one embodiment, a visual indicia is presented to a subject similar to visual indicia presented to the subject in the example of the eye-hand coordination test described above. To test split attention, a second visual indicia is presented in a different location from the first visual indicia, where the subject may be required to identify the first visual indicia while locating the second visual indicia. The second visual indicia may, for example, be a Landolt "C," where the test subject is required to identify the direction orientation of the second visual indicia. The second visual indicia may be presented in the center of a display device, while a first visual indicia testing the subject's eye-hand coordination may be presented on the display device away from the center of the display. One skilled in the art will appreciate and understand that any suitable test of split attention may be used by the split attention component 212.

The reaction time component 214 is configured to test the reaction time of a test subject. Any suitable test may be used and is within the scope of this invention. By way of example, without limitation, a visual indicia may be presented to the test subject. The subject may be required to recognize this first indicia by, for example, using the touch-screen input device to touch the first indicia. Then, a second visual indicia may be displayed or presented to the subject, who then must recognize the second visual indicia by, for example, moving the hand that is touching the first indicia to touch the second indicia. Measuring the time required for a subject to indicate the second indicia after being displayed measures the reaction time of the subject.

The body coordination component 216 is configured to test the body coordination of a subject. One skilled the art will appreciate that any suitable test that tests body coordination may be used. By way of example, without limitation, this component may utilize a balance board to test a subject's body coordination, while administering a vision test simultaneously. Such a test may include presenting a visual indicia in a specified quadrant of a display device, and then requiring the subject to indicate that quadrant by balancing on the board.

Figure 4:
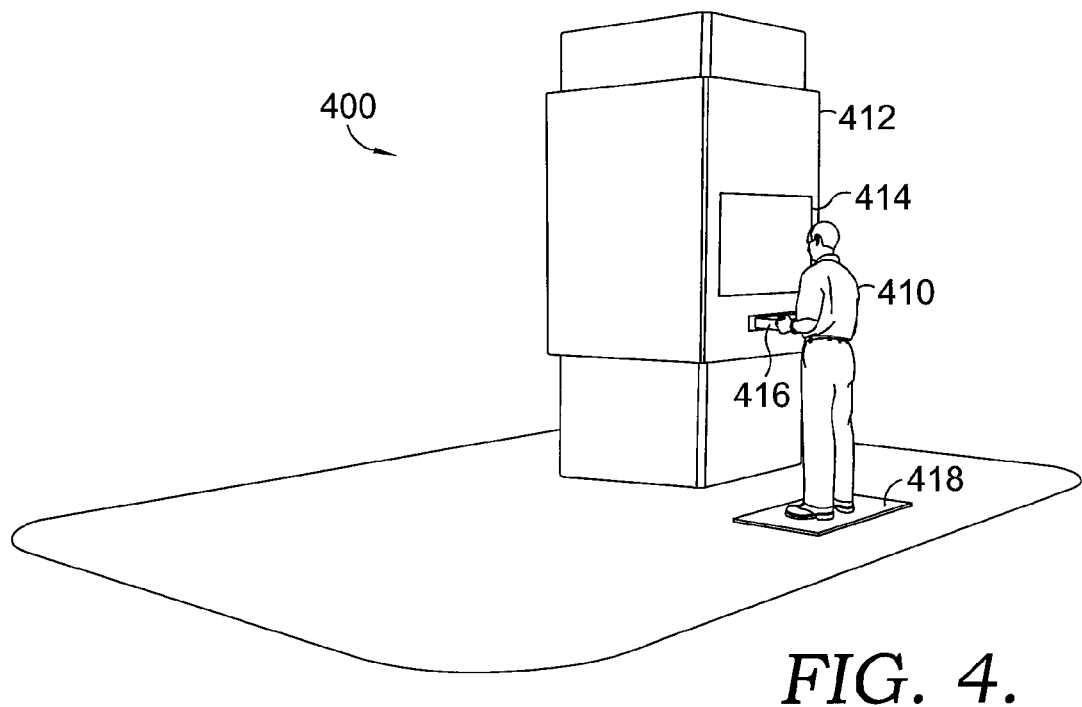
FIG. 4 illustrates an exemplary unitary vision and coordination testing unit, in accordance with an embodiment of the present invention.

Referring now to FIG. 4, an exemplary vision and coordination testing system 400 is illustrated, in accordance with an embodiment of the present invention. A subject 410 participating in testing may use visual testing system 400 to test the visual ability of subject 410 during an activity. Test unit 412 comprises a display device 414 and an input device 416. In this embodiment, the testing unit 412 may receive inputs from subject 410 via input device 416 that is connected (e.g., by a wired or wireless connection) to test unit 412. One skilled in the art will appreciate that subject 410 may provide input to test unit 412 via any type of input device and that subject 412 may interact with input device 416 through any means (e.g., physical interaction, voice recognition) in order to provide the appropriate response. Moreover, this invention contemplates using more than one input device for various tests. For example, in FIG. 4, the subject 410 is illustrated as standing on a balance board 418, which may be used in certain tests, such as the body coordination test described above.

By having a unitary test unit, such as test unit 412, that is capable of presenting several tests to a subject, a better overall evaluation of the subject's vision and coordination abilities may be provided. Further, because test unit 412 may include processing capabilities, it is able to process the data, resulting in a determined score and/or a training regimen for the subject.

Figure 5:
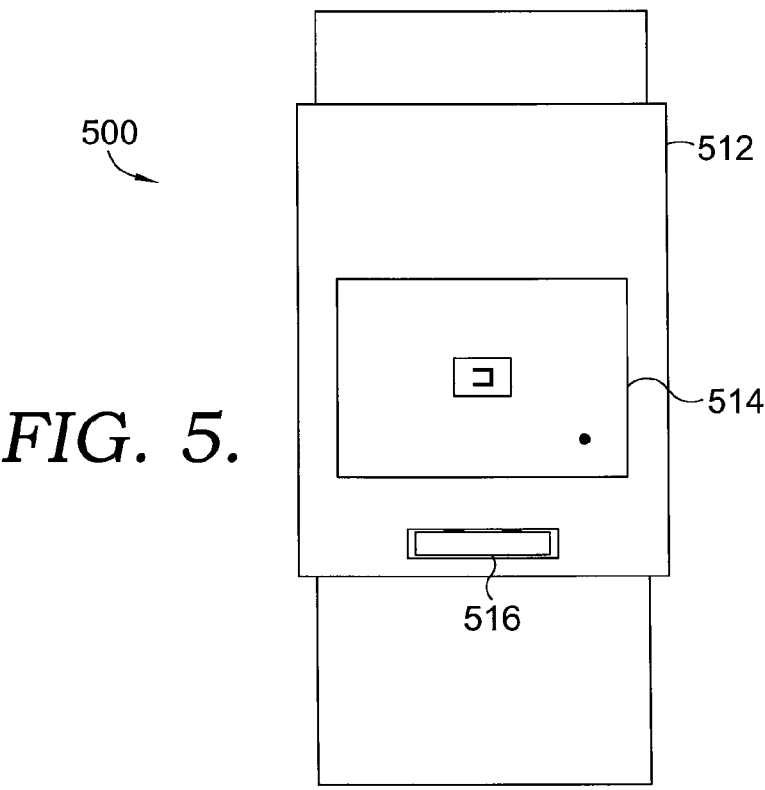
FIG. 5 illustrates another embodiment of a unitary vision and coordination testing unit, in accordance with the present invention.

FIG. 5 illustrates a vision and coordination testing system 500, in accordance with an embodiment of the present invention. The test unit 512 comprises a display device 514 and a an input device 516. The input device 516 shown in FIG. 5 is illustrated as a set of manual buttons; however, any type of input device is contemplated to be within the scope of this invention. In some embodiments, the display device 514 may be touch-sensitive, thereby allowing it to also serve as an input device.

Figure 6:
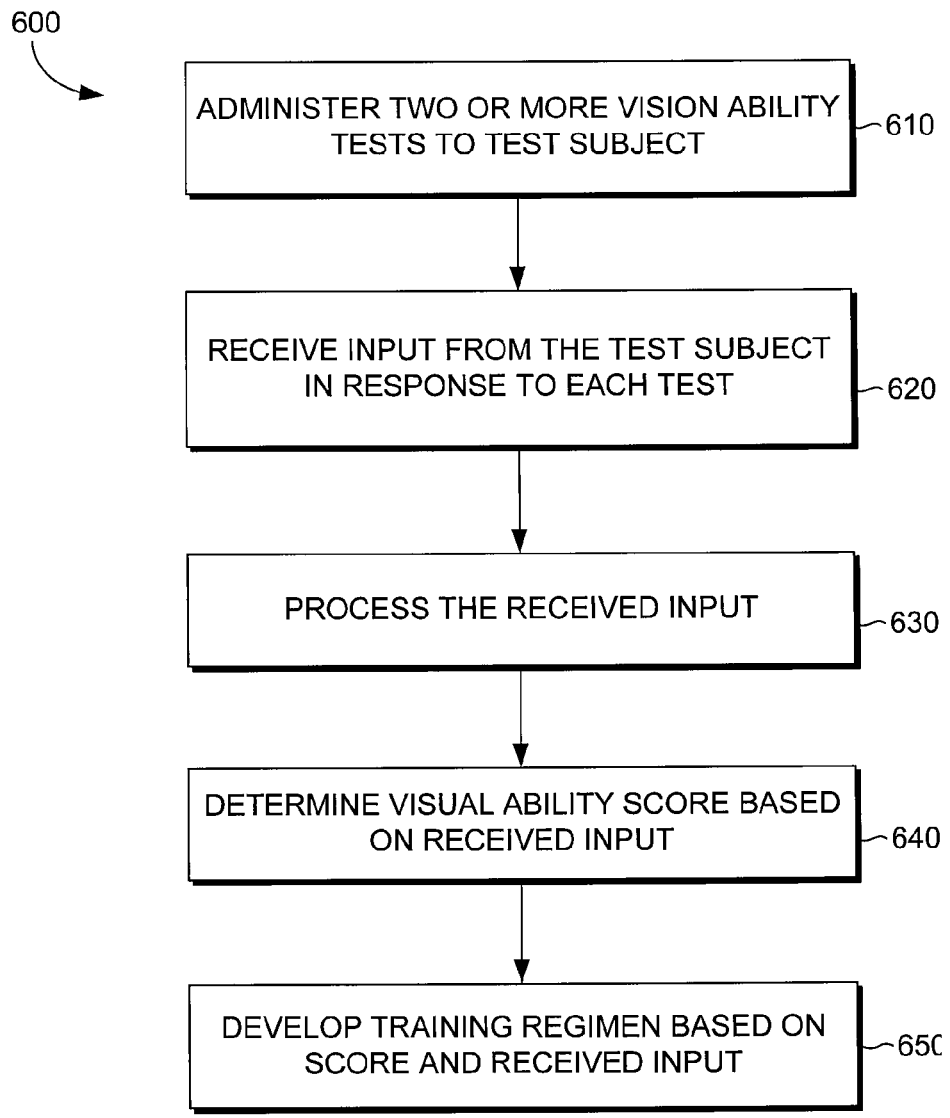
FIG. 6 illustrates a flow diagram showing a method for testing the vision and coordination abilities of a subject at a unitary location, in accordance with an embodiment of the present invention.

Referring now to FIG. 6, a flow diagram 600 is illustrated that shows a method of testing the vision and coordination abilities of a subject. Although the terms "step" and "block" are used hereinbelow to connote different elements of methods employed, the terms should not be interpreted as implying any particular order among or between various steps herein disclosed unless and except when the order of individual steps is explicitly described. Initially, two or more vision and/or coordination tests are administered to a test subject (e.g., utilizing test unit 110 of FIG. 1). This is indicated at block 610. One skilled in the art will appreciate that any of the tests described above may be administered, as well as any other test that measures an individual's vision and coordination abilities. The specific tests administered and the order of the tests may be configured on the subject's ability level, competition level, particular activity, and the like. While the test is administered to the subject, the subject may provide the appropriate response by interacting with an input device that is connected to the test unit via an input component. This is indicated at block 620. Multiple input devices may be used, and more than one input may be received from the subject. For example, during a split attention test, a subject may provide one response to a visual indicia testing eye-hand coordination, while the subject may provide another response to a visual indicia at a separate location, as described above. A processing component (e.g., processing component 118 in FIG. 1) may then process the received input by, for example, collecting the data, determining a score, or developing a training regimen. The data may be stored, for example, in database 104, or sent via a delivery component to, for example, central location 106. This is indicated at block 630.

Optionally, at block 640, the data received from the subject's input with each test may be used to determine a score for the subject. An individual score may be determined for each test, and an overall score may be determined based on the data from all tests. The score may further be based on corresponding data for a particular population, and the subject's score may be compared accordingly (e.g., the subject may be given a percentile of their performance). At block 650, a training regimen may be developed for the test subject to train his or her vision and coordination abilities based on, for example, their determined score and their received input in response to the vision ability tests.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and is within the scope of the claims.

What is claimed is:

1. A device for testing the visual and coordination ability of a subject comprising:
    a presenting component configured to present two or more vision and coordination ability tests, wherein a vision and coordination ability test includes a test that measures both the vision and coordination of a subject, and wherein the subject provides input in response to each test;
    an input component configured to receive the input provided by the subject;
    a processing component configured to process the received input and to determine a score based on the received input; and
    a training development component that provides a vision and coordination training regimen based on the determined score.

2. The device of claim 1, wherein one of the two or more vision and coordination ability tests includes an eye-hand coordination test.

3. The device of claim 2, wherein the eye-hand coordination test comprises a visual indicia presented to the subject that the subject locates by providing an input in response to the location of the visual indicia.

4. The device of claim 1, wherein one of the two or more vision and coordination ability tests includes a split attention test.

5. The device of claim 4, wherein the split attention test comprises a first visual indicia presented to the subject at a first location that the subject provides an input in response to locating the first visual indicia and a second visual indicia presented to the subject at a second location that requires a response from the subject.

6. The device of claim 5, wherein the second visual indicia is a Landolt C.

7. The device of claim 1, wherein one of the two or more vision and coordination ability tests includes a reaction time test.

8. The device of claim 1, wherein the one of the two or more vision and coordination ability tests includes a body coordination test.

9. A method of testing the vision and coordination ability of a test subject, wherein the method occurs at a unitary location, the method comprising:
    administering two or more vision and coordination ability tests to a test subject, wherein a vision and coordination ability test is a test that measures both the vision and coordination of a subject;
    receiving input from the test subject in response to each test;
    processing the received input;
    determining a score based on the received input; and
    providing a vision and coordination training regimen based on the determined score.

10. The method of claim 9, wherein one of the two or more vision and coordination tests includes an eye-hand coordination test.

11. The method of claim 10, wherein the eye-hand coordination test comprises a visual indicia presented to the subject that the subject locates by providing an input in response to the location of the visual indicia.

12. The method of claim 9, wherein one of the two or more vision and coordination ability tests includes a split attention test.

13. The method of claim 12, wherein the split attention test comprises a first visual indicia presented to the subject at a first location that the subject provides an input in response to locating the first visual indicia and a second visual indicia presented to the subject at a second location that requires a response from the subject.

14. The method of claim 13, wherein the second visual indicia is a Landolt C.

15. The method of claim 9, wherein one of the two or more vision and coordination ability tests includes a reaction time test.

16. The method of claim 15, wherein one of the two or more vision and coordination ability tests includes a body coordination test.

17. A method of testing the vision and coordination ability of a test subject, wherein the method occurs at a unitary location, the method comprising:
    administering at least an eye-hand coordination test and a split attention test to a test subject;
    receiving a first input from the test subject in response to the eye-hand coordination test;
    receiving a second input from the test subject in response to the split attention test;
    processing the first input and the second input;
    determining a score based on the processed first input and the processed second input; and
    providing a vision and coordination training regimen based on the determined score.

* * * * *